United States Patent
Dugas et al.

(10) Patent No.: US 6,616,895 B2
(45) Date of Patent: Sep. 9, 2003

(54) SOLID STATE MEMBRANE CHANNEL DEVICE FOR THE MEASUREMENT AND CHARACTERIZATION OF ATOMIC AND MOLECULAR SIZED SAMPLES

(75) Inventors: Matthew P. Dugas, St. Paul, MN (US); Gregory L. Wagner, Roseville, MN (US)

(73) Assignee: Advanced Research Corporation, Minneapolis, MN (US)

( * ) Notice: Subject to any disclaimer, the term of this patent is extended or adjusted under 35 U.S.C. 154(b) by 0 days.

(21) Appl. No.: 09/815,461

(22) Filed: Mar. 23, 2001

(65) Prior Publication Data

US 2002/0025277 A1 Feb. 28, 2002

Related U.S. Application Data

(60) Provisional application No. 60/191,663, filed on Mar. 23, 2000.

(51) Int. Cl.[7] .............................................. G01N 27/06
(52) U.S. Cl. ............... 422/82.01; 422/68.1; 422/82.02; 436/2; 436/72; 436/86; 436/89; 436/151; 435/4; 435/6; 435/287.2; 435/285.2; 435/287.3; 438/49
(58) Field of Search ............................... 436/2, 72, 514, 436/63, 86, 89, 149, 150, 151, 180; 422/50, 68.1, 73, 82.01, 82.02; 438/49; 435/4, 6, 287.2, 285.2, 287.3

(56) References Cited

U.S. PATENT DOCUMENTS

| | | | |
|---|---|---|---|
| 5,795,782 A | | 8/1998 | Church et al. .................. 436/2 |
| 6,287,517 B1 | * | 9/2001 | Ackley et al. ............. 422/68.1 |
| 6,362,002 B1 | * | 3/2002 | Denison et al. ................. 436/2 |
| 6,413,792 B1 | * | 7/2002 | Sauer et al. ................... 438/49 |
| 6,428,959 B1 | * | 8/2002 | Deamer .......................... 435/6 |

* cited by examiner

Primary Examiner—Jill Warden
Assistant Examiner—Sam P. Siefke
(74) Attorney, Agent, or Firm—Dorsey & Whitney LLP

(57) ABSTRACT

A solid state device is formed through thin film deposition techniques which results in a self-supporting thin film layer that can have a precisely defined channel bored therethrough. The device is useful in the chacterization of polymer molecules by measuring changes in various electrical characteristics as molecules pass through the channel. To form the device, a thin film layer having various patterns of electrically conductive leads are formed on a silicon substrate. Using standard lithography techniques, a relatively large or micro-scale aperture is bored through the silicon substrate which in turn exposes a portion of the thin film layer. This process does not affect the thin film. Subsequently, a high precision material removal process is used (such as a focused ion beam) to bore a precise nanoscale aperture through the thin film layer that coincides with the removed section of the silicon substrate.

15 Claims, 10 Drawing Sheets

SOLID STATE MEMBRANE CHANNEL DEVICE FOR THE MEASUREMENT AND CHARACTERIZATION OF ATOMIC AND MOLECULAR SIZED SAMPLES

CROSS REFERENCE TO RELATED APPLICATIONS

The present application is a continuation-in-part of Provisional Application Serial No. 60/191,663, filed Mar. 23, 2000, which is herein incorporated by reference in its entirety.

BACKGROUND OF THE INVENTION

1. Field of the Invention

The present invention relates to a device for the characterization of polymer molecules. More specifically, the present invention relates to a solid state device useful for the characterization of polymer molecules as well as a method of making the same.

2. Description of the Related Art

It has recently been announced that the mapping of the human genome has been completed. This historic development will lead to a myriad of developments ranging from the identification of the genetic basis of various diseases to the formulation and fabrication of new drugs and treatment protocols. All of this will only further serve to increase the already high demand for rapid information processing relating to polymer characterization, particularly that of various nucleic acids (i.e., DNA).

Heretofore, the sequencing of nucleic acids has been performed through chemical or enzymatic reactions. This allows for the nucleic acids to be separated into strains having differing lengths. This is generally tedious and laborious work and requires a significant amount of time and effort to complete. Thus, the results from any desired characterization of a particular polymer sequence are usually quite expensive and take a fair amount of time to obtain.

A significant advancement in the characterization of polymer molecules was introduced by Church et al. in U.S. Pat. No. 5,795,782 which issued on Aug. 18, 1998. Church et al. teach a method of causing polymer molecules, and in particular nucleic acids, to pass through an ion channel in an otherwise impermeable organic membrane. The membrane separates two pools of a conductive fluid solution containing a supply of the polymer material in question. By generating a voltage differential across the membrane, the polymer molecules can be ionized or polarized and guided through the ion channel. By measuring the various electrical characteristics of the membrane, the particular base of the polymer molecule can be identified by identifying the changes in these electrical characteristics as a particular base of the polymer molecule occludes the channel. Thus, each type of base member will exhibit unique characteristics that are identifiable by variations in monitored electrical parameters such as voltage or current.

The drawback of this device is that it is difficult to create an impermeable membrane having a sufficiently small ion channel that will allow the device to function properly. Church, et al. teaches using an organic membrane where an ion channel is created through the membrane via a chemical etching process. This is extremely difficult to do on a cost effective and repetitive scale. Specifically, the formation of an otherwise impermeable organic membrane and chemically etching or otherwise forming the ion channel is a hit or miss operation that may or may not actually produce the appropriately channeled membrane. Thus, while the concept of providing for the rapid determination of the character of polymer molecules is an extremely important one, no device has been provided that can be reliably produced while achieving accurate results.

Therefore, there exists a need to provide a high quality, reliable and easily reproducible polymer characterization device.

SUMMARY OF THE INVENTION

The present invention provides a generally impermeable membrane having a nano-scale aperture. Polymer molecules are caused to travel through the aperture or channel and the electrical characteristics generated by the particular base or monomer occupying the channel at a given time is determined based upon various measurements made by monitoring the membrane.

In one embodiment, the membrane is used to separate two pools of a conductive medium containing quantities of the polymer molecules in question. Unlike membranes used by the previous device which are organic in nature, the membrane of the present invention is inorganic and uses a combination of wafer and thin film technology to accurately and consistently manufacture a membrane having the desired characteristics. The membrane is formed by providing a base preferably using a silicon substrate. A thin film is deposited on one side of the silicon substrate. The thin film includes one or more integrated electrical leads that can ultimately be connected to the testing and monitoring equipment. Using standard lithography techniques and taking advantage of the anisotropic etching characteristics of single crystal silicon wafing, a micro-scale hole is etched through the silicon substrate. In the selected area, the etching process removes all of the silicon substrate but leaves the thin film entirely intact and unaffected. Thus, a self supporting thin film, such as SiN for example is bridged across a micro-scale aperture in a silicon substrate. Using a focused ion beam or electron beam lithography, a nano-scale aperture is precisely cut through the thin film layer. Thus, the nano-scale aperture provides a channel through which polymer molecules pass and are measured in various ways.

The present invention also provides for differing configurations of the thin film layer. At a minimum, a single electrically conductive layer should be provided. If properly configured, the fabrication of the nano-scale aperture will bisect this conductive layer into two independent and electrically isolated conductive members or leads. Thus, as a molecule passes through the channel, monitoring equipment connected to each of the electrically conductive sections can obtain measurements such as voltage, current, capacitance or the like. This would be a transverse measurement across the channel.

In practice, it may be more practical to provide one or more dielectric layers that effectively protect and insulate the conductive layers. The use of such dielectric layers can simplify the manufacturing process and allows for multi-level conductive layering to be generated. That is, providing a single conductive layer or effectively providing electrical leads in a common plane allows for measurements of the particular polymer base in a transverse direction. However, by stacking conductive layers atop on another (electrically isolated from one another such as by an interposed dielectric layer), measurements of certain electrical characteristics can be taken in the longitudinal direction.

The present invention provides for a variety of lead patterns in both a longitudinal and transverse direction. In one embodiment, a single, shaped electrically conductive layer is provided. The conductive layer is relatively narrow near a medial portion so that a channel formed therethrough by a focused ion beam effectively bisects the electrically conductive layer into two electrically independent sections or leads. The benefit of such a construction is a minimal number of steps are required to complete the finished product. However, one potential drawback is that the single conductive layer must be applied relatively precisely in that the channel which eventually separates the layer in two will usually have a diameter on the order of ten nanometers.

Since this level of precision may be difficult in some manufacturing processes, another single layer approach is provided. Namely, a single electrically conductive layer is provided. However, the medial portion need not be so narrow as to allow bisection by the formation of a nano-scale aperture. Thus, when a nano-scale aperture is bored through the thin film layer, electrically conductive material remains which effectively connects the two leads. A focused ion beam or other precision material removing apparatus is used to remove a section of the thin film layer so that the two leads are electrically independent.

By providing leads on a single plane, various transverse measurements of electrical characteristics can be performed. Bisecting a single layer results in the formation of two leads. The present invention also provides for fabricating four or more leads in a single plane so that multiple transverse measurements are possible.

By utilizing dielectric layers, electrically conductive leads can be fabricated in multiple planes. This not only allows for transverse measurements to be made, but facilitates longitudinal measurements as well. Any configuration or variation of the single plane lead structures can be repeated with the multi-level thin film layers. Namely, relatively precise conductive layers can be applied relying on the focused ion beam or other precision cutting device to bisect each respective layer. Alternatively, a focused ion beam or other precision cutting device can be utilized for removing a precise amount of the electrically conductive layer in and around the desired channel area, once again resulting in any number of leads being fabricated in any given plane. Thus, multiple transverse and multiple longitudinal measurements can be made between any given pair of leads.

Longitudinal measurements in and of themselves may be sufficient to determine the necessary characteristics in the polymer material in question. That is, it is not necessary to have electrically isolated lead pairs in a single plane. This allows for an embodiment where a relatively imprecise electrically conductive layer is formed in a first plane. A second relatively imprecise electrically conductive layer is formed in a second plane wherein the second plane is separated from the first by a dielectric layer. By providing a nano-scale aperture through the entirety of the thin film layer (i.e., the dielectric layers and both the conductive layers), a completed structure is fabricated. In this embodiment, electrical measurements are not possible within a single plane. However, by measuring across different planar levels sufficient information may be gathered to characterize the polymer molecule. This configuration provides for relative ease during the manufacturing process and results in a repeatable and highly accurate device.

DETAILED DESCRIPTION OF THE INVENTION

Figure 1:
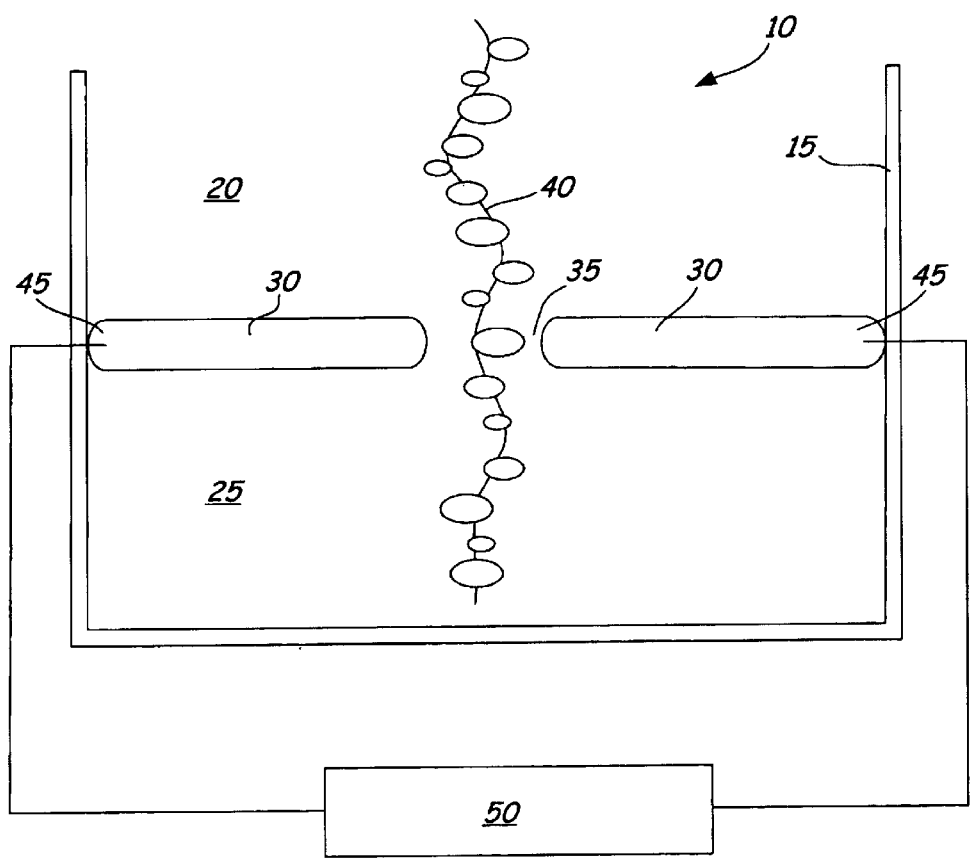
FIG. 1 is a schematic illustration of a membrane separating medium bearing pools containing linear molecules wherein the linear molecules pass through a channel in the membrane and are detected by the attached electronic testing equipment.

Referring to FIG. 1, a channel device is illustrated and generally referred to as 10. Channel device 10 includes container 15 within which resides a volume of fluid. The fluid is separated into an upper pool 20 and lower pool 25 by a membrane 30. The liquid within upper pool 20 and lower pool 25 is preferably a conductive solution and contains a number of linear polymer molecules 40. Polymer molecules 40 are free to travel through the liquid medium contained within container 15. FIG. 1 is provided for illustrative purposes only and the components shown are not drawn to scale in general or with respect to each other.

By using various processes, such as introducing a voltage differential across membrane 30, polymer molecules 40 can be directed through channel 35 in membrane 30. Channel 35 is a nano-scale aperture. Typically, channel 35 will have a diameter of up to about 10 nm and preferably between 2–4 nm. Of course, the actual size will be selected to best serve the desired application. As linear polymer molecule 40 travels through channel 35, the individual monomers will interact with membrane 30 within channel 35. This will result in various electrical and/or physical changes that can be detected by the electronic testing equipment 50 that is interconnected with membrane 30 through leads 45. For example, a given monomer within channel 35 can be determined by changes in measured voltage, conductance, capacitance or various other electrical parameters. Thus, as polymer molecule 40 passes through channel 35, each individual monomer is characterized. As this data is received and stored, the character of the polymer is accurately identified. In previously known devices utilizing this technique, the membrane consists of a difficult to manufacture and delicate organic membrane hopefully having an appropriately sized channel chemically etched therethrough. Fabricating an otherwise impermeable organic membrane is a difficult and inconsistent process. It is even more difficult to chemically create a single or a controlled number of channels therethrough while of course maintaining the proper dimensions in the fabricated channel. Finally, connecting testing equipment and making electrical measurements from such a membrane is exceedingly difficult. Thus, the present invention provides a reliable, mechanically fabricated inorganic membrane 30.

Figure 2A:
FIG. 2A is an end view of a silicon substrate.

FIG. 2A illustrates the first step in the process of fabricating membrane 30. A supportive substrate 55 is provided. Preferably, substrate 55 is a self supporting member constructed of an etchable material. An ideal material is silicon and, in particular, silicon wafers which are widely available and easy to work with. It should be noted that all of the Figures only illustrate components schematically. Thus, the scale imparted bears no relationship to actual practice. Furthermore, the scale of the components as compared to one another is skewed so as to illustrate concepts.

Figure 2B:
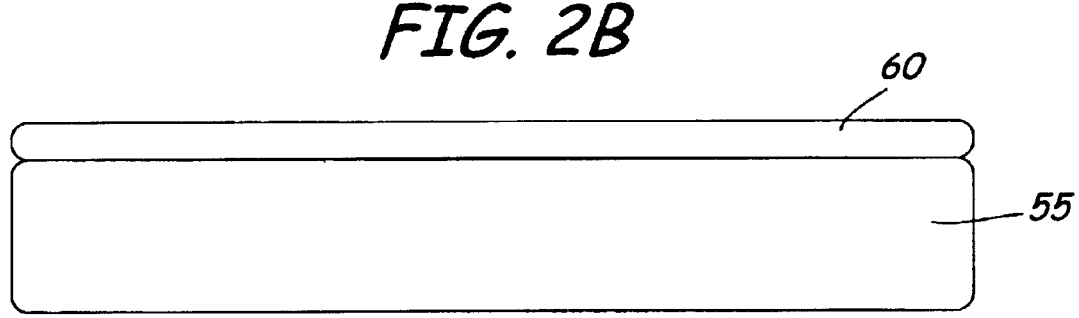
FIG. 2B is an end view of a silicon substrate with a thin film layer applied thereto.
Figure 2C:
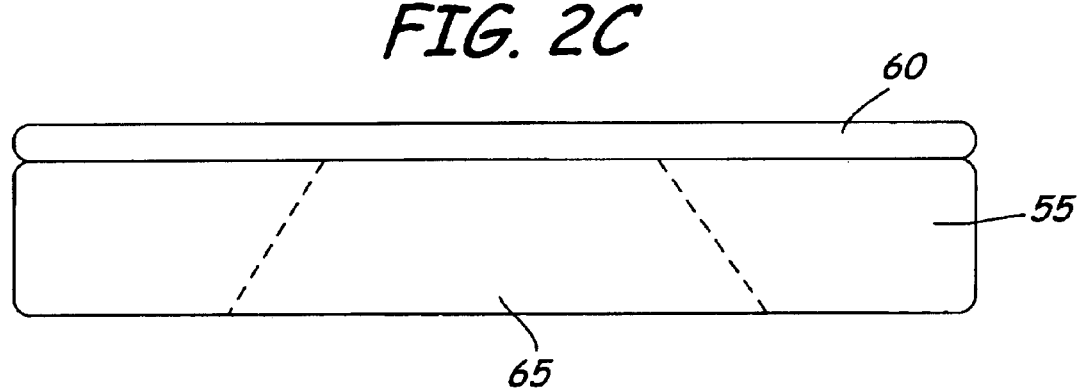
FIG. 2C is a partially sectional end view of a silicon substrate having a lithography hole bored therethrough with a self supporting thin film layer atop the silicon substrate.
Figure 2D:
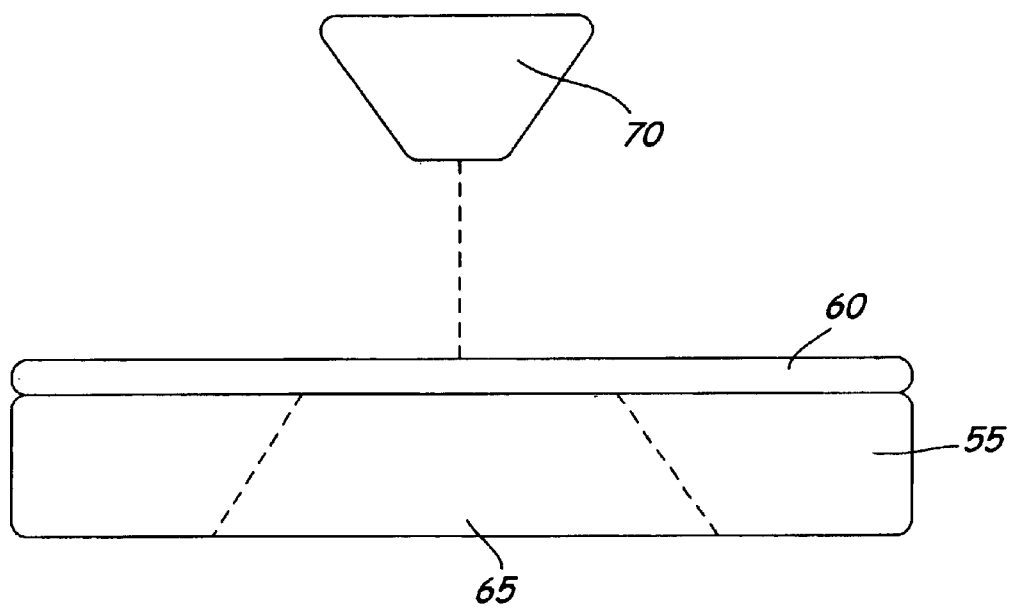
FIG. 2D is a schematic view illustrating the orientation of a focused ion beam used to cut a channel through the thin film layer.
Figure 2E:
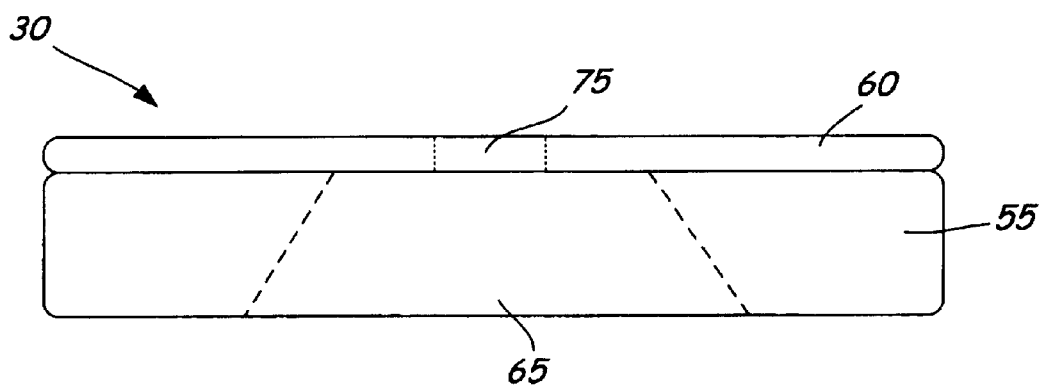
FIG. 2E is a silicon substrate bearing a self supporting thin film layer having a nano-scale channel bored therethrough.

In FIG. 2B, a thin film 60 is deposited on one surface of silicon substrate 55. Thin film 60 is shown as a single layer, however its actual construction can be more complicated and will be explained in greater detail below. After thin film 60 has been generated on silicon substrate 55, a hole 65 is etched into the silicon substrate 55 using standard lithography techniques, such as wet etching. Such techniques will remove the silicon in the desired area but will have no effect on thin film 60. Thus, over the area defined by lithography hole 65, thin film layer 60 becomes self supporting as illustrated in FIG. 2C. Subsequently, a channel 75 (as illustrated in FIG. 2E) is cut through thin film 60 with a focused ion beam (FIB) 70 or other suitable precision milling device such as electron beam lithography, neutral particle beam, charged particle beam, x-ray, or other suitable mechanism.

When using a FIB, the aspect ratio between the thickness of the thin film and the size of the channel 75 must be considered. That is, a FIB can only mill so deep while maintaining a particular diameter channel. Typical FIB devices have an optimal range of about 1:2, and are functional to about 1:4. Thus, the thickness of this film 60 should be selected to be in accordance with the limitations of the FIB (or the alternative milling device) actually being utilized. Thus, for a channel 75 having an approximate diameter of 10 nm, an optimal thin film 60 thickness would be less than 20 nm (1:2) to less than 40 nm (1:4). The result as illustrated in FIG. 2E is a completed membrane 30 having a base or silicon substrate 55 with a relatively large (microscale) lithography hole 65 on top of which resides a partially self supporting thin film layer 60 having a nano-scale aperture or channel 75 bored therethrough. As illustrated, channel 75 and lithography hole 65 are aligned so that passage through channel 75 is in no way impeded by any portion of the remaining silicon substrate 55. As explained in greater detail below, thin film layer 60 has electrically conductive portions which may be coupled to testing equipment. This may be accomplished by providing a conductive thin film layer on one or both sides of self supporting membrane 60. Thus, various electrical characteristics of thin film 60 can be monitored by the testing equipment. When membrane 30 as illustrated in FIG. 2E is actually used in a polymer molecule characterization device 10, thin film layer 60 effectively acts as the membrane, as silicon substrate 55 is essentially a support member. Depending upon the fluid medium selected, it may be desirable to provide additional material around silicon substrate 55 to protect it. For example, Teflon® or other suitable materials could be utilized.

Figure 3:
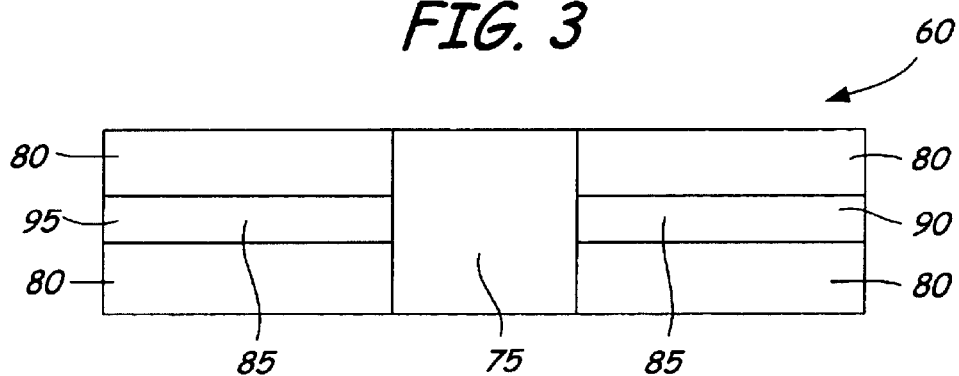
FIG. 3 is a sectional view of a thin film layer having a conductive layer disposed between two dielectric layers.

Referring to FIG. 3, thin film 60 is shown in more detail. FIG. 3 is a sectional view of a multi-layer thin film having electrically conductive layer 85 disposed between two nonconductive or dielectric layers 80. Channel 75 effectively serves to isolate the electrically conductive layer 85 into two discrete sections thus forming right lead 90 and left lead 95. Thus, by appropriately monitoring right lead 90 and left lead 95 with the appropriate testing equipment, the characteristic of objects that pass through channel 75 can be determined by their effect on these electrical characteristics. All of this assumes that a satisfactory signal to noise ratio (SNR) can be achieved for the particular objects in question. Of course, for ease of manufacturer, the configuration could be reversed, that is layers of conductive material could sandwich the dielectric self supporting structure. Or, a single conductive layer (split into two leads) could be formed on either side of the self supporting dielectric layer. Such a configuration is illustrated in FIG. 4B. A silicon substrate 91 includes a partially self supporting silicon nitride layer 92. Two conductive layers 93, 94 are deposited, one on either side of layer 92. This provides a simple lead structure that allows longitudinal measurements.

Figure 4:
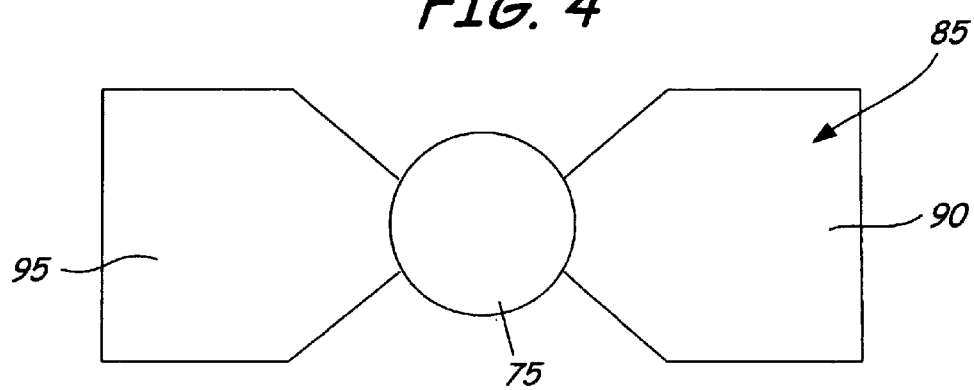
FIG. 4 is a top view of a conductive layer having two leads with a nano-scale channel bored therethrough.
Figure 4A:
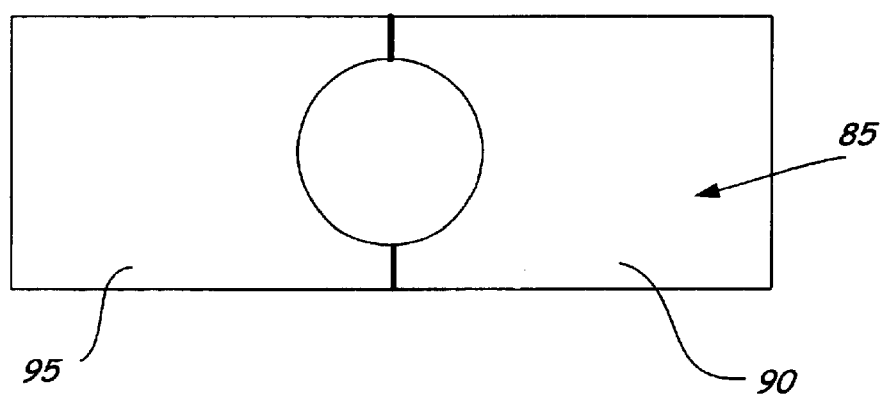
FIG. 4A is a top view of a conductive layer having two leads with a nano-scale channel bored therethrough.
Figure 4B:
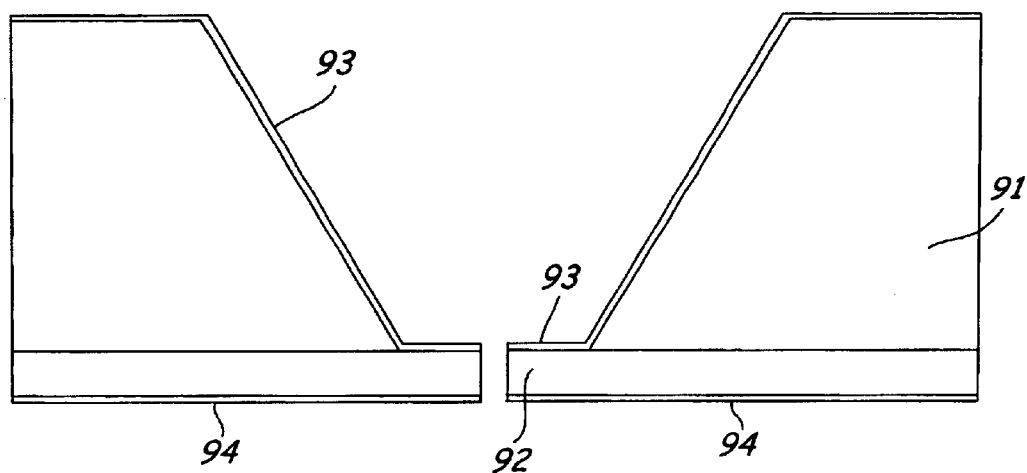
FIG. 4B is a side elevational view of a silicon substrate with a partially self supporting layer sandwiched between two conductive layers.

FIG. 4 is a top view illustrating conductive layer 85 as it is separated into right lead 90 and left lead 95 by channel 75. As illustrated, right lead 90 and left lead 95 are physically separated from one another by the diameter of channel 75. During the fabrication of thin film 60, this lead and channel configuration can be generated in a variety of ways. To begin with, a dielectric layer 80 is applied through a sputtering or other deposition technique. Subsequently, conductive layer 85 is applied in an appropriate pattern. Such a pattern can be that of FIG. 5 or FIG. 6. Alternatively, as illustrated in FIG. 4A, a single conductive layer 85 can be applied and then split into two separate leads 90, 95 by cutting or otherwise separating conductive layer 85.

Figure 5:
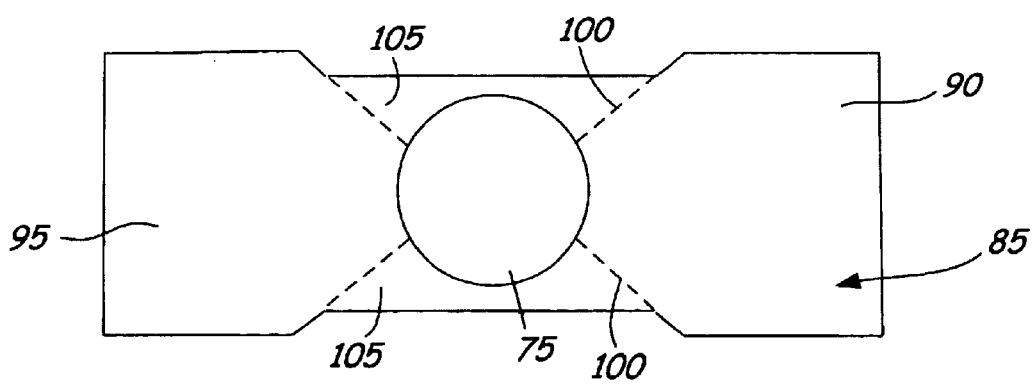
FIG. 5 is a top view of an electrically conductive layer having two leads and a nano-scale aperture bored therethrough wherein dashed lines are used to indicate excess material that must be removed to electrically isolate the two leads from one another.

Referring to FIG. 5, the initial application of conductive layer 85 results in a pattern that cannot be bisected merely by cutting channel 75 with a focused ion beam. Thus, to produce right lead 90 and left lead 95, the area defined by FIB pattern 100 must be removed by an appropriate technique. A focused ion beam can be used to precisely eliminate those portions of conductive layer 85 designated as removed area 105. While this requires additional milling steps, it is not as time intensive as milling channel 75 since the thickness of the conductive layer is relatively small. Other appropriate material removal techniques could be utilized so long as they can be defined precisely enough to result in the electrical isolation of right lead 90 from left lead 95 as illustrated in FIG. 4.

Once right lead 90 and left lead 95 have been so defined, a subsequent layer of dielectric material 80 may be applied completing the fabrication of thin film layer 60. The use of the various dielectric layers 80 provides for some electrical insulation between adjacent electrically conductive members and also serves to protect the leads from physical contact or abrasion. The specific patterning or arrangement of the various dielectric layers 80 is optional so long as the resulting thin film layer 60 includes electrically conductive leads that can be connected to the appropriate testing equipment and which are capable of detecting the necessary electrical characteristics of the molecules passing through channel 75.

Figure 6:
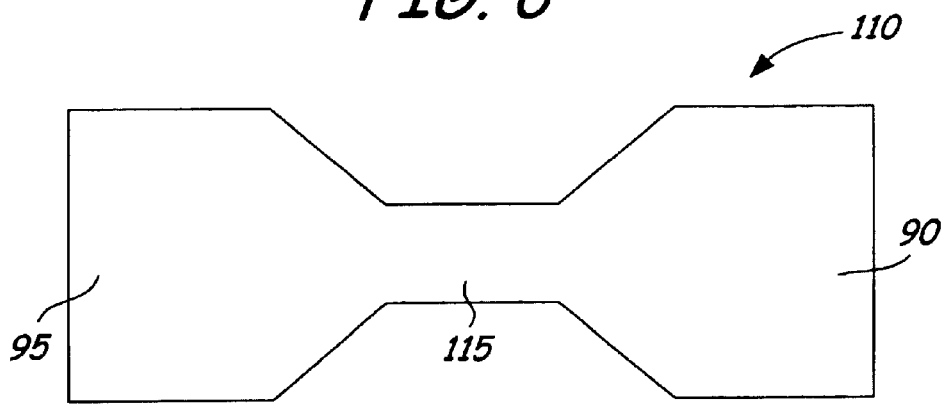
FIG. 6 is a top view of a shaped, electrically conductive layer.

FIG. 6 illustrates an alternative pattern for initially forming conductive layer 85 as conductive layer 110. As illustrated, conductive layer 110 provides for an enlarged right lead 90 and an enlarged left lead 95 interconnected by a channel area 115. The precise dimensions of channel area 115 are selected so that it is effectively removed when channel 75 is cut therethrough by a focused ion beam, effectively electrically isolating right lead 90 from left lead 95. Of course, the same effect could be achieved by applying right lead 90 and left lead 95 as separate elements with no interconnection during the deposition process. In either case, sufficient precision must be maintained so that when channel 75 is created, right lead 90 and left lead 95 while electrically isolated from one another are in contact with or relatively close to the outer perimeter of channel 75 so as to be properly effected by molecules passing through channel 75. It may be desirable to have the edge of the leads end prior to channel 75 so that they are not in direct contact with the fluid medium and the polymer molecules during testing. This results in a small section of dielectric material between the edge of the leads and channel 75. Such a modification would simply require additional milling of the conductive layer or that an appropriate initial pattern be applied.

Figure 7:
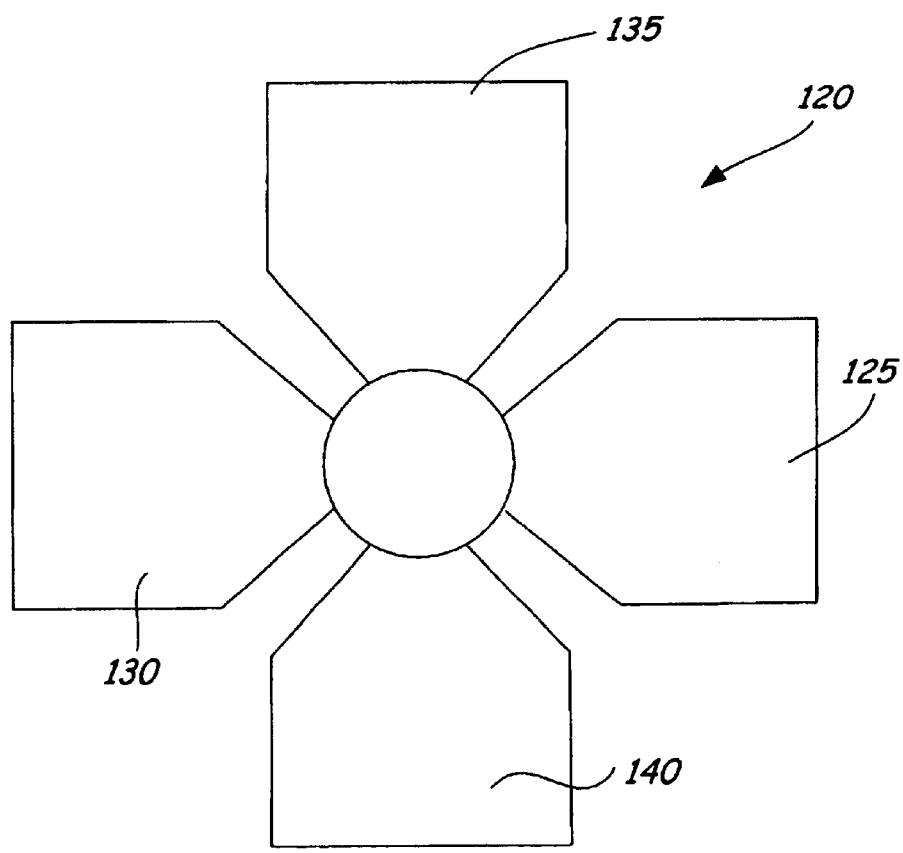
FIG. 7 is a top view of an electrically conductive layer separated into orthogonal lead pairs with a nano-scale aperture bored therethrough.

FIG. 7 illustrates a quadrapole arrangement of orthogonal lead pairs 120. Orthogonal lead pairs 120 include right lead 125, left lead 130, upper lead 135, and lower lead 140. All four leads are electrically isolated from one another and abut the perimeter of channel 75. As described above, the leads can instead terminate prior to contacting channel 75. The same techniques used for forming conductive layer 85 of FIG. 4 are applicable to forming orthogonal lead pairs 120. The benefit of providing orthogonal lead pairs 120 is that multiple transverse measurements can be made of the molecules passing through channel 75. Thus, measurements are not limited to a single pair of leads. By comparison of the output from any two lead pairs additional data can be obtained about the molecule passing therethrough.

Figure 8:
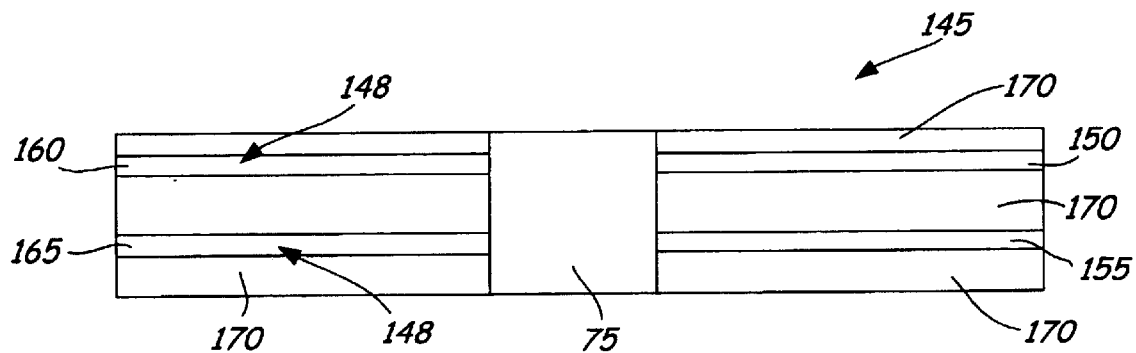
FIG. 8 is a sectional view of a thin film layer having dual electrically conductive layers.

FIG. 8 illustrates a dual conductive layer thin film 145. As illustrated, various conductive layers 148 are disposed between various dielectric layers 170 to form this configuration. Once again, it is the orientation of the conductive layers that is important. The particular configuration chosen for the dielectric layers 170 will depend largely upon the selected deposition technique as well as the desired level of resultant protection. In the embodiment shown in FIG. 8, a dielectric layer 170 is disposed between the lower conductive layer and the silicon substrate (not shown). Additionally, another dielectric layer 170 is disposed above the top conductive layer. Finally, a third layer of dielectric material 170 is disposed between the two conductive layers which may be necessary to achieve the desired level of electrical isolation. Thus, this series of conductive layers results in a right upper lead 150, a right lower lead 155, a left upper lead 160, and a left lower lead 165 as viewed through a sectional view. The conductive leads abut the outer perimeter of channel 75. Optionally, the leads could terminate prior to contacting channel 75. Thus, as a molecule passes therethrough, the resultant change in various electrical characteristics can be detected by the appropriate testing equipment connected to the various leads. Once again, transverse measurements can be made (i.e., measuring across from right upper lead 150 to left upper lead 160). Additional transverse measurements can be made by measuring across right lower lead 155 to left lower lead 165. However, the dual conductive layer thin film 145 allows for various longitudinal measurements to be made as well. That is, measuring across right upper lead 150 to right lower lead 155 and/or left upper lead 160 to left lower lead 165. The introduction of longitudinal measurements allows for another degree of measurement on the various polymer molecules passing therethrough. Voltage and channel current can be measured in the longitudinal direction. While two conductive layers have been illustrated, more can be introduced as desired.

Figure 9:
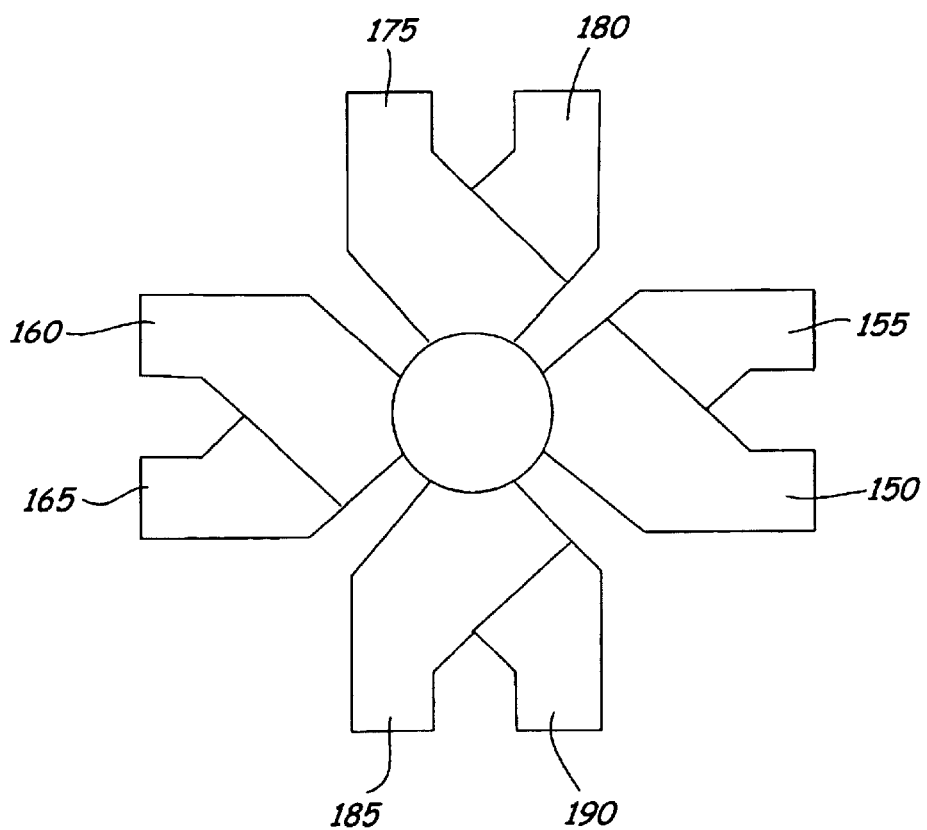
FIG. 9 is a top view of the conductive layers forming the dual conductive layer thin film of FIG. 8.

FIG. 9 illustrates quadrapole orthogonal lead pairs and a dual conductive layer thin film structure. That is, four leads are provided which are electrically independent from one another and abutting channel 75 in a common plane. An additional four leads are provided which are electrically isolated from one another as well as from the first four leads. The second four leads exist in a second plane, separate and spaced apart from the first, and electrically isolated therefrom. More specifically, in a first plane, right upper lead 150, front upper lead 185, left upper lead 160, and back upper lead 175 form a first set of orthogonal lead pairs. Disposed in a parallel plane beneath the first, right lower lead 155, front lower lead 190, left lower lead 165, and back lower lead 180 form a second set of orthogonal lead pairs. This configuration provides a large number of independent measurements that can be made in both the transverse and longitudinal directions. That is, any two lead pairs can be monitored and compared. In addition, multiple measurements can be made by comparing multiple combinations of various lead pairs.

The previously explained embodiments are advantageous in that they allow for a maximum range of measurement possibilities. One potential drawback is the complexity of the lead patterns and the thin film layers. Specifically, the various leads must either be deposited in a very accurate manner, or accurate leads must be defined by a precision material removal process such as using a focused ion beam. In either event, the fabrication of the thin film layer can be complex.

Figure 10:
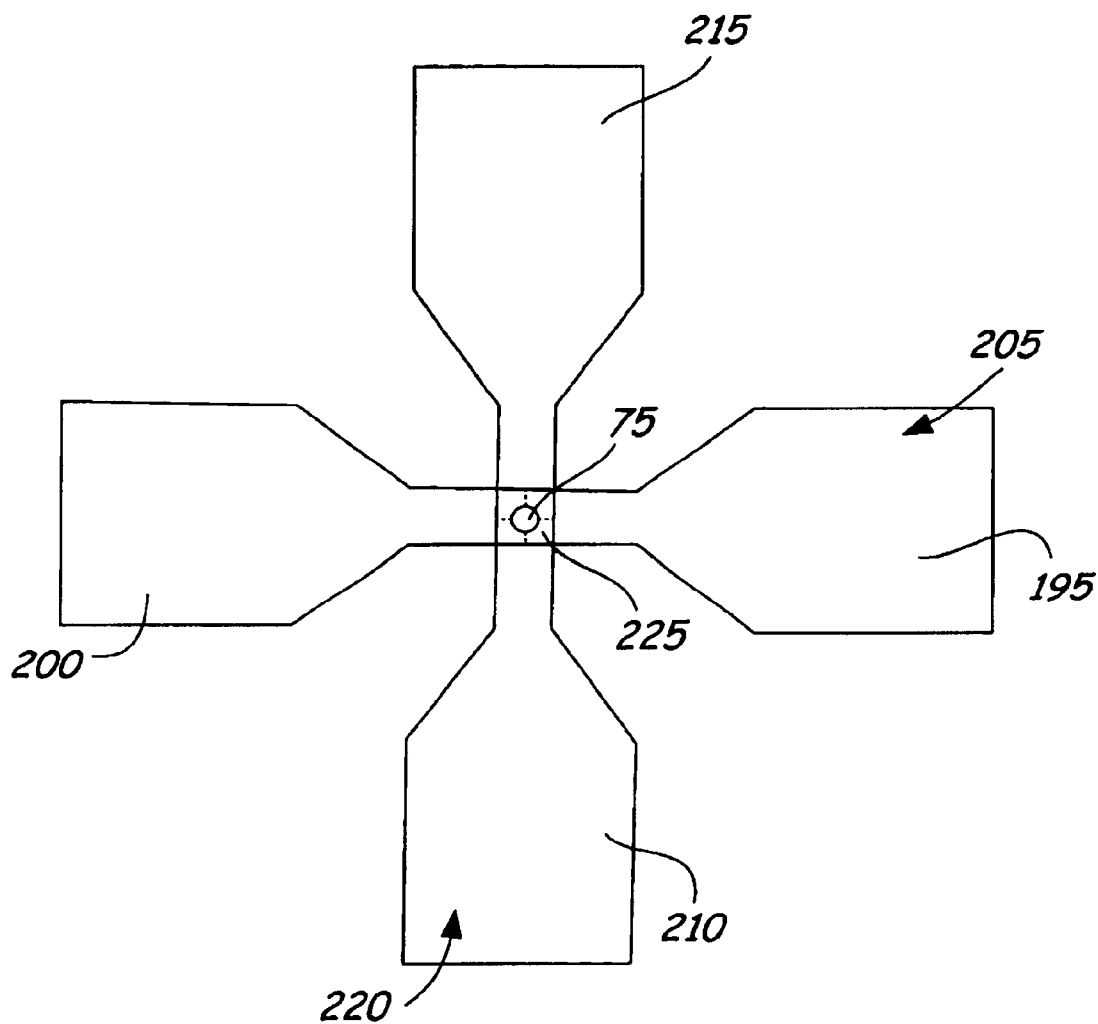
FIG. 10 is a top view of two electrically conductive layers one atop another with a nano-scale channel board therethrough.

FIG. 10 illustrates a configuration where only longitudinal measurements can be made between leads existing in different, electrically isolated planes. Longitudinal measurements alone can provide sufficient information to characterize the molecule. As illustrated, an upper layer 205 of the electrically conductive material is disposed above a lower layer 220 of electrically conducted material. Though not shown, upper layer 205 and lower layer 220 are separated by a sufficient amount of dielectric material to assure electrical isolation. A channel 75 is cut through both upper layer 205 and lower layer 220 as well as any existing dielectric layers. Thus, as before, passage of polymer molecules is allowed through channel 75. Upper layer 205 includes right lead 195 and left lead 200. Likewise, lower layer 220 includes front lead 210 and back lead 215. Channel 75 is cut through these respective layers at an area of intersection 225 where upper layer 205 overlaps lower layer 220. Since only longitudinal measurements are to be made with this configuration, the precision of the previous embodiments is no longer required. Specifically, channel 75 need not electrically isolate right lead 195 from left lead 200. Similarly, channel 75 need not electrically isolate front lead 210 from back lead 215. The only measurements that can be made are in a longitudinal direction. For example, measuring across front lead 210 to right lead 195. Measurements in the transverse direction are no longer possible in that right lead 195 is not electrically isolated from left lead 200, since a significant amount of electrically conductive material still exists around channel 75. The same configuration occurs in lower layer 220. Thus, it should become readily apparent that longitudinal measurements can be made between either lead of upper layer 205 to either lead of lower layer 220. Thus, it should be further apparent that one lead of each layer is effectively redundant and need not actually be created. The configuration illustrated in FIG. 10 takes into account that it may be easier to simply apply certain patterns using thin film deposition techniques even though a portion of that conductive layer may in effect be unnecessary. In any event, all that is required is that an electrically conductive member exists in a first plane electrically isolated from another electrically conductive member located in a second plane. Furthermore, a channel 75 must be bored through each conductive layer (or in close proximity thereto) and any dielectric material existing therebetween. Thus, the particular configuration or pattern of the selected leads can be selected as desired. What results is a relatively easy thin film configuration to fabricate, thus allowing for a polymer molecule characterization device to be manufactured with a high degree of precision on a cost effective basis.

To allow the embodiment of FIG. 10 to make transverse measurements, upper layer 205 and lower layer 220 need only be separated (each into two leads) as indicated by the dotted lines.

Figure 11:
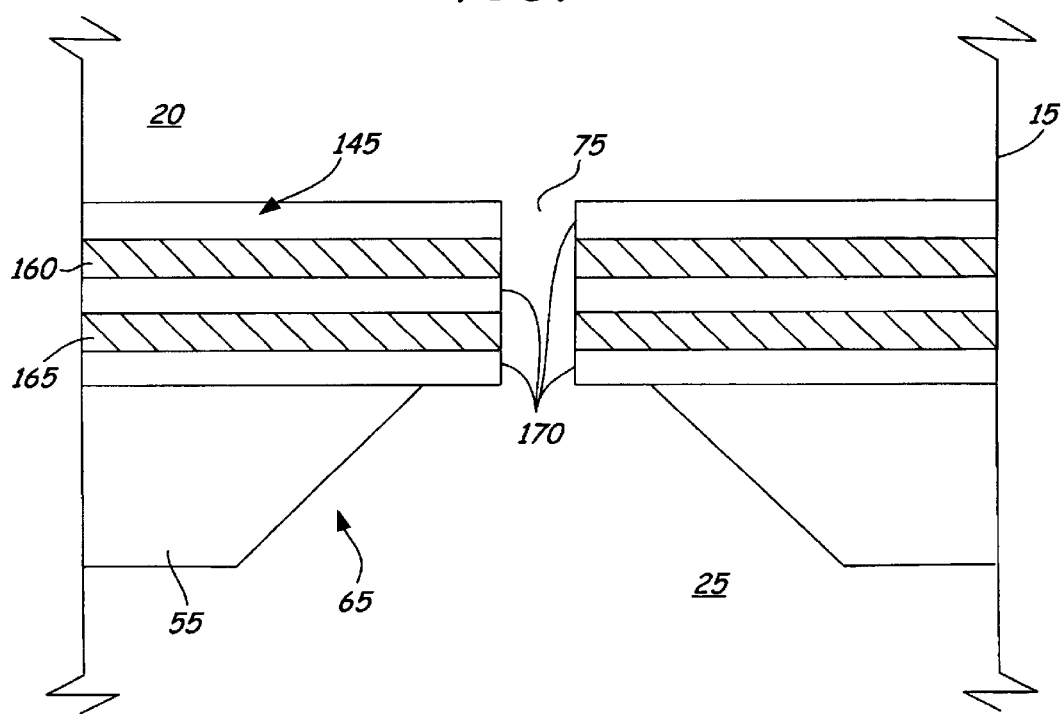
FIG. 11 is a schematic illustration of a dual conductive layer thin film and a silicon substrate forming a membrane separating an upper and lower medium bearing liquid.

FIG. 11 schematically illustrates how a completed polymer characterization device, utilizing a dual conductive layer thin film 145, would appear in a sectional view. Dual conductive layer thin film 145 is attached to silicon substrate 55 having a lithography hole 65. Dual conductive layer thin film 145 essentially forms a self supporting member in the area formed by lithography hole 65. Within the area where dual conductive layer thin film 145 forms a self supporting member, channel 75 is bored therethrough. Thin film 145 effectively separates upper pool 20 from lower pool 25. Using various known methods, such as applying a voltage differential across thin film 145, polymer molecules in one pool can be directed into the other. As they pass therethrough, they will effect the electrical characteristics of thin film 145 and these variations will be detected by taking measurements in a transverse direction. That is, for example, from right upper lead 150 to left upper lead 160 or right lower lead 155 to left lower lead 165. Alternatively measurements in a longitudinal direction could be made, such as by taking measurements across right upper lead 150 to right lower lead 155 or from left upper lead 160 to left lower lead 165. Of course additional measurements could be made from leads on opposite sides of channel 175 which are also located in separate planes. The configuration illustrated in FIG. 11 will also be applicable to the dual layer orthogonal lead pairs illustrated in FIG. 9.

Figure 12:
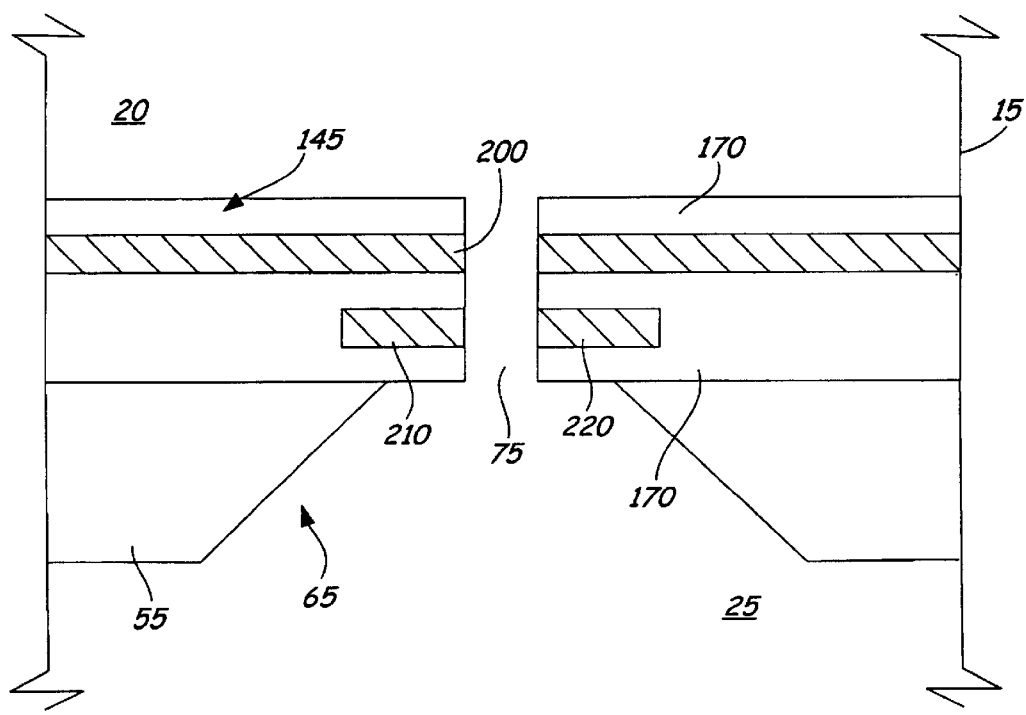
FIG. 12 is a schematic illustration illustrating a thin film having dual conductive layers coupled with a silicon substrate separating an upper and lower medium bearing pool.

FIG. 12 illustrates the use of a simplified dual conductive thin film 145 which only allows for measurements in a longitudinal direction. That is FIG. 12 is illustrative of the pattern illustrated in FIG. 10 in a completed application. Measurements can be made from either right lead 195 or left lead 200 to either of front lead 210 or back lead 215 (not illustrated).

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited in the particular embodiments which have been described in detail therein. Rather, reference should be made to the appended claims as indicative of the scope and content of the present invention.

To obtain proper paragraph numbering after paragraph 99, use Heading 2 for the appropriate style.

What is claimed is:

1. A device for the characterization of polymer molecules, comprising:

a substrate forming a base of the device, the substrate including an aperture therethrough;

having a nano-scale thickness disposed on the substrate and extending across the aperture so that the thin film is self supporting over an area defined by the aperture;

a nano-scale channel through the thin film in the area defined by the aperture, wherein the channel is sized so as to allow passage of polymer molecules therethrough one at a time so that as a polymer molecule passes therethrough a given monomer will cause a detectable change in the thin film wherein the detectable change will characterize the monomer.

2. The device of claim 1, further comprising a container for holding a fluid medium having a quantity of polymer molecules disposed therein, wherein the substrate including the thin film is disposed within the container and divides the fluid medium into a first pool and a second pool wherein polymer molecules are directed from the first pool through the channel and into the second pool by generating a voltage differential across the thin film.

3. The device of claim 1, further comprising:

a first electrically conductive layer disposed within the thin film so as to form a first set of electrically independent leads, wherein each lead has a first end and a second end and the first end of each lead is proximate the channel.

4. The device of claim 3 wherein the first end of each lead of the first set forms a portion of a perimeter of the channel.

5. The device of claim 3 wherein the first set of electrically independent leads comprises two leads positioned on opposite sides the channel.

6. The device of claim 3 wherein the first set of electrically independent leads comprises four leads positioned evenly around the channel in a quadrapole arrangement.

7. The device of claim 3, further comprising:

a second electrically conductive layer disposed within the thin film so as to form a second set of electrically independent leads, wherein each lead has a first end and a second end and the first end of each lead is proximate the channel.

8. The device of claim 7 wherein the first set of leads is separated from the second set of leads by a dielectric layer.

9. The device of claim 7 wherein the first end of each lead of the second set forms a portion of a perimeter of the channel.

10. The device of claim 7 wherein the second set of electrically independent leads comprises two leads positioned on opposite sides the channel.

11. The device of claim 7 wherein the second set of electrically independent leads comprises four leads positioned evenly around the channel in a quadrapole arrangement.

12. The device of claim 1, further comprising:
- a first electrically conductive layer disposed within the thin film so as to form a first electrical lead;
- a second electrically conductive layer disposed within the thin film so as to form a second electrical lead, wherein the second electrically conductive layer is separated from the first electrically conductive layer by a dielectric layer, so that the channel is formed to pass through the first electrically conductive layer, the dielectric layer and the second electrically conductive layer.

13. The device of claim 1 where the substrate is silicon.

14. The device of claim 1 wherein the aperture has micro-scale dimensions and the channel has nano-scale dimensions.

15. The device of claim 1 wherein the channel has a diameter less than approximately 10 nm.

* * * * *

UNITED STATES PATENT AND TRADEMARK OFFICE
CERTIFICATE OF CORRECTION

PATENT NO. : 6,616,895 B2 Page 1 of 1
DATED : September 9, 2003
INVENTOR(S) : Matthew P. Dugas and Gregory L. Wagner It is certified that error appears in the above-identified patent and that said Letters Patent is hereby corrected as shown below:

Column 10,
Line 20, currently reads "having a nano-scale thickness disposed on the substrate", and should read -- a thin film having a nano-scale thickness disposed on the substrate -- therefor.

Signed and Sealed this

Eleventh Day of May, 2004

JON W. DUDAS
*Acting Director of the United States Patent and Trademark Office*